United States Patent [19]

Rydell

[11] Patent Number: 6,110,171
[45] Date of Patent: Aug. 29, 2000

[54] ELECTROSURGICAL CUTTING AND COAGULATING INSTRUMENT FOR OPEN SURGERY

[75] Inventor: Mark A. Rydell, Golden Valley, Minn.

[73] Assignee: Everest Medical Corporation, Minneapolis, Minn.

[21] Appl. No.: 09/264,785

[22] Filed: Mar. 9, 1999

[51] Int. Cl.[7] .................................................. A61B 18/18
[52] U.S. Cl. .................................. 606/51; 606/50; 606/48
[58] Field of Search ............................ 606/41, 45, 47–51

[56] References Cited

U.S. PATENT DOCUMENTS

| | | | |
|---|---|---|---|
| 5,190,541 | 3/1993 | Abele et al. | 606/46 |
| 5,472,442 | 12/1995 | Klicek | 606/42 |
| 5,603,712 | 2/1997 | Koranda et al. | 606/51 |
| 5,735,849 | 4/1998 | Baden et al. | 606/51 |

*Primary Examiner*—Michael Peffley
*Attorney, Agent, or Firm*—Nikolai, Mersereau & Dietz, P.A.

[57] ABSTRACT

A bipolar electrosurgical cutting and coagulating instrument for cutting and coagulating tissue in open surgery. The instrument comprises a handle member from which an electrically conductive first forceps rod and an electrically conductive second forceps rod extend in opposing relationship to each other. An electrically conductive wire extends from the handle member to reside within a longitudinal lumen of the second forceps rod. The first forceps rod is partially movable proximally within the handle member wherein a movable electrical conduit resides. Proximal movement of the first forceps rod causes the rod to contact and move the conduit which, in turn, causes distal movement of the conductive wire with which the conduit is in contact. Such distal wire movement causes the distal end of the wire to extend distally from the second forceps rod. When the wire is extended, the distal end thereof functions as a scalpel since bipolarity is established between the distal end of the wire and the second forceps rod. When the wire is retracted, a coagulation mode results since bipolarity is established between the first and second forceps rods.

9 Claims, 1 Drawing Sheet

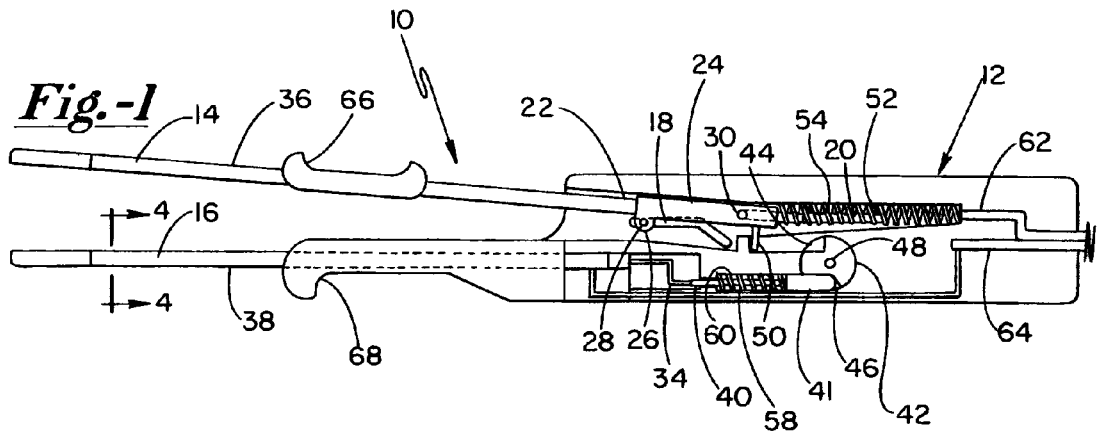
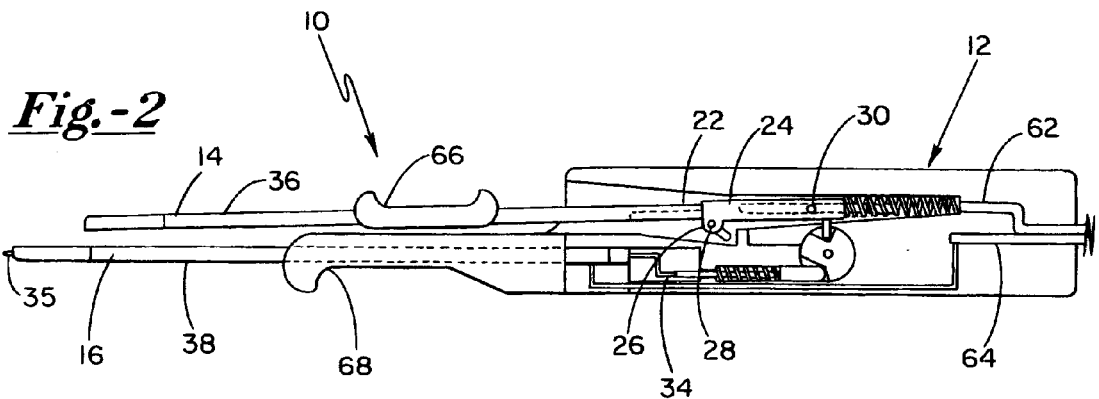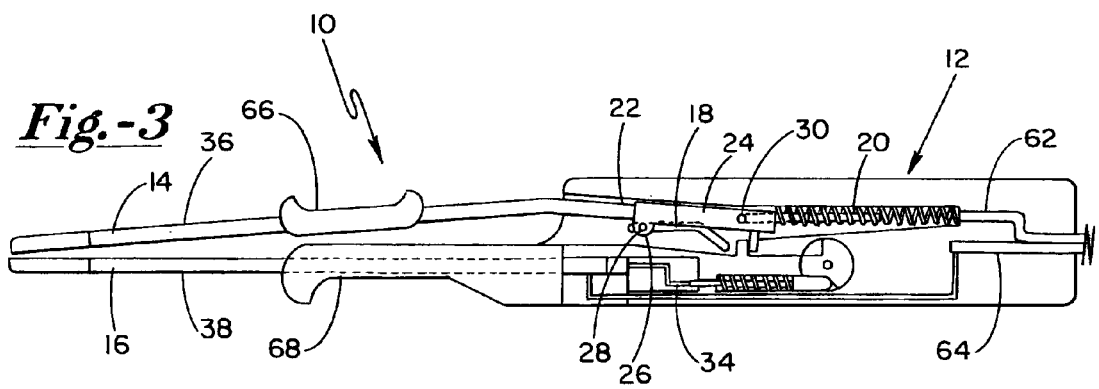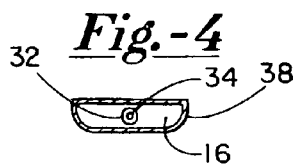

6,110,171

ELECTROSURGICAL CUTTING AND COAGULATING INSTRUMENT FOR OPEN SURGERY

BACKGROUND OF THE INVENTION

This invention relates in general to bipolar electrosurgical instruments, and in particular to a bipolar electrosurgical instrument for open surgery and having both cutting and coagulating properties.

The benefits of bipolar electrosurgical instruments are well recognized within the medical profession. In particular, a bipolar instrument provides a physician with greater control over the location of electrical activity within a patient during a surgical procedure. As opposed to a monopolar device, which requires a base plate electrode usually situated at a remote location from the surgery site and therefore requiring passage of current through a portion of the body of the patient, a bipolar device confines electrical activity at the site of the surgical procedure.

While electrosurgical scalpels and electrosurgical coagulating forceps are presently available, a single bipolar instrument which permits a physician to selectively cut or coagulate tissue can provide much greater versatility in achieving timely treatment in electrosurgical procedures.

It is therefore a primary object of the present invention to provide an electrosurgical instrument for open surgery which is capable of cutting and coagulating tissue to be so treated.

Yet another object of the present invention is to provide an electrosurgical instrument for open surgery which permits a user to select a cutting action or a coagulation action.

Still another object of the present invention is to provide an electrosurgical instrument for open surgery wherein one electrode activates a cutting wire and one forceps jaw paddle of the two paddle coagulation forceps, while another electrode activates the second jaw paddle to thereby create bipolarity.

These and other objects of the present invention will become apparent throughout the description thereof which now follows.

SUMMARY OF THE INVENTION

The present invention is a bipolar electrosurgical cutting and coagulating instrument specifically designed for use in cutting or coagulating tissue during open surgery. The instrument comprises a handle member from which a flexible, electrically conductive first forceps rod and a electrically conductive second forceps rod extend in opposing relationship to each other. Both the first and second rods are electrically insulated from each other except at their respective distal ends, and are in contact proximally with a standard high frequency generator to thereby establish bipolarity between their distal ends. The second rod has a longitudinal lumen therethrough in which resides an electrically conductive wire. The wire is insulated for nearly all of its length, with only its distal end being free of insulation. This distal end resides within the distal end of the lumen of the second rod when the wire is in a retracted configuration. Within the handle member is an electrically conductive, movable, conduit in contact with the wire and selectively in contact with an electrically conductive portion of the first rod. The first rod is partially longitudinally movable proximally within the handle member to thereby contact the conduit and simultaneously move the conduit. Movement of the conduit is translated to movement of the wire to thereby cause the distal end of the wire to extend distally beyond the distal end of the second rod. This event further causes a portion of the electrical energy from the first rod to be diverted to the wire and thereby establishes bipolarity between the distal end of the wire and the distal end of the second rod. Although current continues to flow to the first rod, its distance from the distal end of the second rod prevents bipolarity therebetween.

During open surgery, a surgeon has a choice of a tissue cutting function or a tissue coagulation function by manipulating the first rod. Specifically, by moving the first rod proximally the operator extends the distal end of the wire and thereby has the functionality of an electrosurgical scalpel. Subsequently, by returning the first rod to its original position, the operator can move the flexible first rod toward the second rod to thereby establish a bipolar tissue coagulation action at the distal ends of the first and second rods. In this manner, a single instrument provides both tissue severing and tissue coagulating utilities.

BRIEF DESCRIPTION OF THE DRAWINGS

A presently preferred embodiment is illustrated in the accompanying drawings in which:

FIG. 1 is a side elevation view partially in section of a bipolar cutting and coagulating instrument for open surgery;

FIG. 2 is a side elevation view partially in section of the instrument of FIG. 1 in a cutting mode;

FIG. 3 is a side elevation view partially in section of the instrument of FIG. 1 in a coagulating mode; and FIG. 4 is a cross section view along line 4—4 of FIG. 1.

DETAILED DESCRIPTION OF A PREFERRED EMBODIMENT

Referring to FIGS. 1–3, a bipolar cutting and coagulation instrument 10 for open surgery is shown. The instrument 10 comprises a plastic handle member generally designated as 12, from which an electrically conductive first forceps rod 14 and an electrically conductive second forceps rod 16 extend distally. The rods 14, 16 are preferably constructed of stainless steel and are each provided with respective plastic finger grips 66, 68 which permit hand operation of the instrument 10. The finger grip 68 is an extension of the handle member 12. While the distal ends of the rods 14, 16 are electrically active, the remainder of the rods 14, 16 are insulated as with respective Teflon® sheaths 36, 38. The first rod 14 is partially movable proximally within the handle member 12 along a first guide track 18 and a second guide track 20, as depicted in FIG. 2. The proximal end 22 of the first rod 14 is fitted with a metal sleeve 24 having extending therefrom a flange 26 through which a first guide pin 28 passes for residence in the track 18. A second guide pin 30 extends laterally from the sleeve 24 to reside in the second track 20. Cooperation of the guide pins 28, 30 within the respective tracks 18, 20 permits longitudinal movement of the first rod 14 within the handle member 12. Electrical leads 62, 64 leading from a standard high frequency generator (not shown) provide current flow to the respective rods 14, 16. Within the second rod 16 a lumen 32 as shown in FIG. 4 extends longitudinally for the entire length of the rod 16. An electrically conductive wire 34 extends from the handle member 12 through the lumen 32 to terminate at its distal end when retracted within the distal end of the second rod 16. All but the distal end of the wire 34 is electrically insulated as with a Teflon® sheath. The proximal end of the wire 34 is fitted with a metal sleeve 40 having a terminal metal cap member 41.

Situated within the handle member 12 is an electrically conductive conductor roller 42 preferably constructed of stainless steel and rotatable on an axis 48. The roller 42 is provided with an upper cut-out portion 44 and a lower cut-out portion 46. The sleeve 24 at the proximal end of the first rod 14 has a vertical arm 50 which engages the upper cut-out 44 of the roller 42 when the first rod 14 is moved proximally. The sleeve 40 at the proximal end of the wire 34 is engaged with the lower cut-out 46. An upper spring 52 resides within an upper cavity 54 of the handle member 12, and is in kinetic contact with the sleeve 24. A lower spring 58 residing within a lower cavity 60 of the handle member 12 is in kinetic contact with the interior of the cap 41.

Operation of the instrument 10 proceeds through hand manipulation of the first rod 14 with the thumb of an operator. FIG. 1 illustrates the instrument 10 in a "ready" position. If the operator wishes to use the instrument 10 as a scalpel, he or she moves and maintains the first rod 14 downwardly and rearwardly, as shown in FIG. 2, to cause the guide pins 28, 30 to travel proximally within their tracks 18, 20. Simultaneously, such movement places the vertical arm 50 of the sleeve 24 in the upper cut-out 44 of the roller 42 and rotates the roller 42. Such rotation causes the lower cut-out 46 of the roller 42 to push the cap 41, and thus the wire 34, distally to thereby expose the distal end 35 of the wire 34 distally from the lumen 32 in the second rod 16. Current emanating from the first rod 14 powers the wire 34 by passage through the roller 42, while the second rod 16 is powered directly from the high frequency generator, to thereby establish bipolarity between the distal end 35 of the wire 34 and the second rod 16. Such bipolarity provides electrosurgical-scalpel functionality to the distal end 35 of the wire 34. Upon cessation of tissue severing procedures, the operator releases the finger grip 66 of the first rod 14. The springs 52, 58 force the instrument 10 to its initial configuration as shown in FIG. 1.

FIG. 3 illustrates the instrument 10 in a coagulating mode wherein the distal ends of the first and second rods 14, 16 function as bipolar forceps. Specifically, the first rod 14 is forced toward the second rod 16, thereby causing the first rod 14 to flex and bring together the distal ends of the first and second rods 14, 16. Bipolarity exists between the two distal ends which resultantly function as electrosurgical forceps for coagulating tissue. Thus, the instrument 10 can function as both a tissue severing instrument and a tissue coagulating instrument.

While an illustrative and presently preferred embodiment of the invention has been described in detail herein, it is to be understood that the inventive concepts may be otherwise variously embodied and employed and that the appended claims are intended to be construed to include such variations except insofar as limited by the prior art.

What is claimed is:

1. A bipolar electrosurgical instrument comprising:
   (a) first and second conductive rods having proximal and distal ends, each with a conductive forceps jaw at said distal ends, said second conductive rod being tubular with a lumen extending longitudinally therethrough;
   (b) an elongated wire having an insulating covering over substantially its entire length, except at a distal end portion thereof, said wire being disposed in said lumen and reciprocally movable therein between an extended and a retracted position; and
   (c) means for alternately applying a voltage between the distal end portion of the wire and the forceps jaw on the first conductive rod when the distal end portion of the elongated wire is in the extended position and between the conductive forceps jaws on the first and second conductive rods when the distal end portion of the elongated wire is in the retracted position.

2. The bipolar electrosurgical instrument as in claim 1 and further including:
   (a) a handle affixed to the proximal end of the second conductive rod, with the first conductive rod being longitudinally movable within the handle between a retracted and extended position.

3. The bipolar electrosurgical instrument as in claim 2 and further including:
   (a) a coupling member responsive to movement of the first conductive rod to the retracted position for moving the distal end portion of the elongated wire to its extended position.

4. The bipolar electrosurgical instrument as in claim 3 wherein the coupling member is responsive to movement of the first conductive rod to its extended position to move the distal end portion of the elongated wire to its retracted position.

5. A bipolar electrosurgical cutting and coagulating instrument for open surgery comprising:
   (a) a handle member;
   (b) an electrically conductive first forceps rod movable proximally partially within the handle member and an electrically conductive second forceps rod, with each of said rods having a proximal end and a distal end and extending from the handle member in opposing relationship to each other;
   (c) an electrically conductive wire having a proximal end and a distal end and extending from the handle member whereby the distal end of the wire is disposed in a longitudinal lumen within the second forceps rod;
   (d) means for delivering high frequency energy to the first forceps rod and second forceps rod; and
   (e) an electrical conduit disposed within the handle member, said conduit in contact with the proximal end of the conductive wire and in contact with the proximal end of the first forceps rod when said rod is moved proximally within the handle member, said conduit additionally being movable within the handle member from the movement of the first forceps rod, with such movement of the conduit translated to the conductive wire and resultant movement of the wire distally a sufficient distance to expose the distal end of the wire distally from the second forceps rod.

6. A bipolar electrosurgical cutting and coagulating instrument as claimed in claim 5 wherein the proximal end of the first forceps rod is in communication with at least one guide track disposed within the handle member for guiding the proximal movement of the first forceps rod within the handle member.

7. A bipolar electrosurgical cutting and coagulating instrument as claimed in claim 5 wherein the electrical conduit is a roller rotatable on an axis, said roller having a lower cut-out portion in communication with the proximal end of the conductive wire and an upper cut-out portion, with the proximal end of the first forceps rod in communication with the upper cut-out portion when the first forceps rod is moved proximally to thereby rotate the roller and move the conductive wire distally.

8. A bipolar electrosurgical cutting and coagulating instrument as claimed in claim 7 wherein a first spring means is in contact with the proximal end of the first forceps rod and a second spring means is in contact with the proximal end of the conductive wire, with said first and second spring means situated in kinetic cooperation to urge the first forceps rod distally and the conductive wire proximally.

9. A bipolar electrosurgical cutting and coagulating instrument as claimed in claim 8 wherein a finger grip is situated on the first forceps rod for finger engagement and movement of the first forceps rod.

* * * * *